United States Patent [19]

Lyon et al.

[11] Patent Number: 4,675,450
[45] Date of Patent: Jun. 23, 1987

[54] PRODUCTION OF CYCLOHEXYL HYDROPEROXIDE

[75] Inventors: John B. Lyon, Orange; Gerald T. Stowe, Victoria, both of Tex.

[73] Assignee: E. I. Du Pont de Nemours and Company, Wilmington, Del.

[21] Appl. No.: 796,738

[22] Filed: Nov. 12, 1985

[51] Int. Cl.[4] ............................................. C07C 45/33
[52] U.S. Cl. .................................... 568/360; 568/570; 568/836
[58] Field of Search ............... 568/342, 360, 570, 575, 568/836

[56] References Cited

U.S. PATENT DOCUMENTS

| 2,851,496 | 9/1958 | Cates et al. | 260/586 |
| 3,510,526 | 5/1970 | Bonnart et al. | 260/586 |
| 3,530,185 | 9/1970 | Pugi | 260/586 |
| 3,917,708 | 11/1975 | Kuessner et al. | 260/586 |
| 3,923,895 | 12/1975 | Costantini et al. | 568/342 |
| 3,949,004 | 4/1976 | Sorgenti et al. | 568/331 |
| 3,957,876 | 5/1976 | Rapoport et al. | 260/586 |
| 3,987,100 | 10/1976 | Barnette et al. | 260/586 |
| 4,115,207 | 9/1978 | Murtho | 568/342 |
| 4,341,907 | 7/1982 | Zelonka | 568/360 |
| 4,465,861 | 8/1984 | Hermolin | 568/342 |

FOREIGN PATENT DOCUMENTS

| 0063961 | 11/1982 | European Pat. Off. | |
| 45-6005 | 2/1970 | Japan | 568/342 |

Primary Examiner—James H. Reamer

[57] ABSTRACT

Production of cyclohexyl hydroperoxide during the cobalt catalyzed oxidation of cyclohexane is enhanced by conducting the oxidation in the presence of a phosphate ester.

3 Claims, No Drawings

PRODUCTION OF CYCLOHEXYL HYDROPEROXIDE

BACKGROUND OF THE INVENTION

1. Field of the Invention

This invention relates to a process for oxidizing cyclohexane with a gas containing molecular oxygen whereby adipic acid precursors are prepared in a manner which permits improved yield of adipic acid. More specifically, this invention relates to a process for oxidizing cyclohexane with a gas containing molecular oxygen, such as air, in the presence of a cyclohexane soluble cobalt catalyst and a phosphate ester to enhance the production of cyclohexyl hydroperoxide.

2. Description of the Prior Art

Adipic acid, among its other uses, is a well known intermediate in the manufacture of nylon, typically being used to react with hexamethylene diamine to form hexamethylene diammonium adipate which is polymerized by removal of water. Historically, adpic acid is usually prepared by the nitric acid oxidation of a mixture of cyclohexanone and cyclohexanol obtained from the oxidation of cyclohexane with a gas containing molecular oxygen, usually air, and optionally in the presence of a catalyst such as a cyclohexane-soluble cobalt compound. During this latter reaction, which is generally operated at low conversions in order to maximize the yield of cyclohexanone (K) and cyclohexanol (A), there is also produced cyclohexyl hydroperoxide (CHHP) which, depending on the oxidation conditions, is converted to K and A during the oxidation or in a separate step is decomposed to or converted to K and A.

One difficulty encountered in the oxidation of cyclohexane, particularly the catalytic oxidation, is that the CHHP is not only readily decomposed to K and A, but also to undesirable by products such as CO, butane, monobasic acids, aldehydes, and the like.

In view of the above there is an incentive to maximize the CHHP produced in the oxidation of cyclohexane by avoiding its decomposition to K and A in that step and the attendant undesirable by product formation, and to decompose or convert the CHHP to K and A in a separate step under nonoxidizing, and less severe thermal conditions than those encountered in cyclohexane oxidation.

Processes for the production of CHHP during the oxidation of cyclohexane have previously been suggested.

Cates, et al., U.S. Pat. No. 2,851,496, disclose a process in which cyclohexane is oxidized with molecular oxygen, optionally in the presence of up to 5000 ppm of a cobalt-containing or chromium-containing catalyst, to provide a mixture containing K, A and CHHP. The resulting CHHP is subsequently decomposed to K and A by heating in the presence of a decomposition catalyst.

Pugi, U.S. Pat. No. 3,530,185, discloses a staged process for oxidizing cyclohexane, with or without catalyst, in which a mixture of gases containing oxygen is introduced into a stream of cyclohexane to give primarily K and A with lesser amounts of CHHP. In general, if catalyst is present the CHHP tends to be decomposed and the main products of the oxidation are K and A.

Rapoport, et al., U.S. Pat. No. 3,957,876, disclose a process for oxidizing cyclohexane to preferentially produce CHHP in which a cyclohexane-soluble cobalt salt, such as those contemplated in this invention, is used as catalyst, and the reaction is carried out in a series of zones. CHHP produced, as measured by the weight ratio of CHHP/(CHHP+K+A), is greater than 0.15.

Barnette, et al., U.S. Pat. No. 3,987,100 disclose an improvement in the Pugi and Rapoport et al. processes wherein cyclohexane is oxidized in the presence of a cyclohexane-soluble binary catalyst system comprising chromium and cobalt salts. The CHHP formed during the reaction is decomposed to K and A in the presence of the binary catalyst.

None of these known processes deal with the possibility of using a phosphorus compound during the oxidation step. However, others have suggested the use of phosphate salts prior to or during the oxidation of cyclohexane.

Bonnart, et al., U.S. Pat. No. 3,510,526, disclose a process for obtaining a high proportion of CHHP by the air oxidation of cyclohexane in the absence of catalyst in apparatus previously rendered passive by treatment with sodium pyrophosphate.

Kuessner, et al., U.S. Pat. No. 3,917,708, disclose a process for producing high yields of K and A by oxidizing cycloalkane in the presence of heavy metal salt oxidation catalyst, such as cobalt monoalkylphosphate or cobalt dialkylphosphate. Production of CHHP is not mentioned.

Sipos, European Patent Application No. 0063931, discloses a process for the oxidation of cycloparaffins, such as cyclohexane, using a binary catalyst system of a cobalt compound and a chromium compound. The cobalt compound may be a dialkylphosphate, and in particular cobalt bis[di(2-ethylhexyl)phosphate]. Free dialkyl phosphate, e.g., di(2-ethylhexyl)phosphate, may be present in the oxidation catalyst. However, enhanced CHHP production is not achieved with the binary catalyst system.

Zelonka, U.S. Pat. No. 4,341,907 discloses a process for oxidation of cycloparaffins, such as cyclohexane, using a catalyst system comprising a cobalt compound in combination with a heterocyclic nitrogen compound, such as pyridine. The cobalt compound is preferably cobalt bis[di(2-ethylhexyl)phosphate]. Significant enhanced CHHP production is not obtained with the phosphate ligand present in the stoichiometric quantity suggested.

SUMMARY OF THE INVENTION

The present invention provides an improvement in a process for the oxidation of cyclohexane to a product fluid consisting essentially of unreacted cyclohexane, cyclohexanone, cyclohexanol and a high proportion of cyclohexyl hydroperoxide, wherein a fluid containing cyclohexane and a cyclohexane soluble catalyst selected from the group consisting of cobalt naphthenate, cobalt octoate, cobalt laurate, cobalt palmitate, cobalt stearate, cobalt linoleate, cobalt acetylacetonate and mixtures thereof is oxidized at a temperature in the range of 130°–180° C. by means of a gas containing molecular oxygen in the presence of an ester of phosphoric acid having the formula

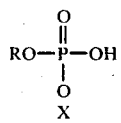

wherein R equals $C_4$-$C_{12}$ alkyl radicals or $C_5$-$C_8$ cycloalkyl radicals and X equals H or R.

The cyclohexane to be oxidized must contain the cobalt catalyst in an amount of about 0.1–5 parts cobalt per million (ppm) parts of product fluid as it exits the oxidizer, that is the fluid containing unreacted cyclohexane, K, A, CHHP and other oxidation products. The amount of catalyst is critical in that amounts in excess of 5 ppm tend to excessively decompose the CHHP, and with amounts less than 0.1 ppm the reaction becomes inefficient. It is essential that the cobalt catalyst be intimately associated with the cyclohexane during the course of the oxidation, and for this reason soluble cobalt salts of carboxylic acids should be used, such as the naphthenate, octoate, laurate, palmitate, stearate, linoleate or acetylacetonate. The octoate and naphthenate are preferred. Other oxidation catalysts, such as the chromium compounds present in the binary catalyst systems of the prior art, should be avoided since they tend to decompose the CHHP.

The other essential ingredient to achieve enhanced CHHP production is the phosphate ester. It should have the formula

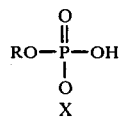

wherein R is selected from the group consisting of $C_4$-$C_{12}$ alkyl radicals and $C_5$-$C_8$ cycloalkyl radicals, and X equals H or R. Such esters include the monobutyl, dibutyl, mon(2-ethylhexyl), di(2-ethylhexyl), monododecyl, didodecyl, monododecyl monocyclopentyl and dicyclooctyl ester of phosphoric acid. The preferred ester is di(2-ethylhexyl)phosphoric acid. It is essential that the phosphate ester be present during the oxidation reaction in an amount sufficient to provide at least 3 acid equivalents (expressed as —OH) per atom of cobalt (Co). The ratio of —OH/Co can be as high as 8/1, however, the preferred range of —OH/Co is 3–5/1 since little additional enhanced CHHP production is achieved above that range. For —OH/Co ratios in excess of 8/1, the catalytic activity of the cobalt catalyst is suppressed to an undesirable level.

DETAILED DESCRIPTION OF THE INVENTION

The process may conveniently be carried out in a tower oxidizer containing a series of zones in which cyclohexane is fed downwardly through the zones and an oxidizing gas containing molecular oxygen, such as air, is passed upwardly through the zones. Such a process is disclosed in Rapoport, et al., U.S. Pat. No. 3,957,876, which disclosure is hereby incorporated by reference in the present application.

The cobalt catalyst and the phosphate ester are usually dissolved in cyclohexane prior to their addition to the oxidation reaction. They may be premixed to give the desired ratio of —OH/Co, or they may be added separately. The only requirement is that they are present during a substantial portion of the oxidation reaction, and prior to any significant decomposition of CHHP. Because the monoesters of phosphoric acid have twice the acid equivalents of the diesters, better control of the reaction can be obtained if the monoester is added separately from the cobalt catalyst and at a point after the catalyzed oxidation reaction has commenced.

In each of the examples set forth in Table 1 a 6 cm by 66 cm 316 stainless steel column was used containing seven sieve trays equally spaced 7.6 cm from each other. Cyclohexane was fed to the top of the column at a rate of 55–65 cc/min. Air was fed equally to the lower five trays through spargers at a rate of 2.5 liters/min. Nitrogen was fed to the bottom of the column at the rate of 0.5 liters/min. A catalyst solution of cobalt octoate in cyclohexane was injected into the cyclohexane feed stream at a rate to maintain the cobalt level at the range indicated in the Table of 0.4–0.6 ppm based on the product fluid exiting the column. In Examples 1–4 and A–C, di(2-ethylhexyl)phosphoric acid was premixed with the cobalt octoate solution in an amount to give the desired —OH/Co ratio. In Examples 5 and D and E, di(2-ethylhexyl)phosphoric acid, and in Example 6 a mixture of mono and di(2-ethylhexyl)phosphoric acid was separately injected into the column at the fourth tray from the bottom in an amount to provide the indicated —OH/Co ratio. Temperatures indicated were maintained by steam tracing and pressure was maintained between 10.9–13.9 atms (160–200 psig) by a pressure control valve at the top of the reactor.

Examples 1–6 are examples of the practice of this invention. The phosphate ester used in Example 6 was EMPHOS PS 400 containing 7.4 mol % phosphoric acid, 57.4 mol % mono(2-ethylhexyl)phosphoric acid and 35.2 mol % di(2-ethylhexyl)phosphoric acid. Examples A–E are presented for comparative purposes.

In each of the Examples set forth in Table 2, a 1 liter stainless reaction vessel, jacketed for steam heating and agitated with a turbine impeller driven by a magnetically coupled motor was used. Gases were added below the impeller and exited the reactor through a double pipe heat exchanger cooled to 8° C. The condensed liquids were returned to the reactor. In each Example, 750 ml of cyclohexane was charged to the reactor and the reactor was sparged with 1.6 liters per minute of nitrogen while heating the liquid to 160° C., maintaining a pressure of 170 psig. After reaching 160° C., the gas was switched to a blend containing 8% oxygen in nitrogen and sufficient cobalt octoate (Examples F, 7 and 8) or cobalt napthenate (Examples G and 9) was added with a syringe pump to produce a 0.5 ppm concentration of cobalt in the solution. In comparative Examples F and G no phosphate ester was added. In Examples 7 and 9 di(2-ethylhexyl)phosphate was added along with the cobalt. In Example 8, EMPHOS, as used in Example 6, was added with a syringe pump five minutes after the cobalt addition. The phosphates were added in an amount to give the desired —OH/Co ratio.

TABLE 1

| | Examples | | | | | | | | | | |
|---|---|---|---|---|---|---|---|---|---|---|---|
| | A | 1 | 2 | B | C | 3 | 4 | D | E | 5 | 6 |
| Catalyst Conc. ppm Co | 0.46 | 0.48 | 0.48 | 0.53 | 0.55 | 0.58 | 0.53 | 0.60 | 0.60 | 0.59 | 0.61 |
| Ester Conc. ppm | 0.0 | 10.5 | 20.9 | 0.0 | 5.6 | 10.9 | 15.4 | 0.0 | 6.7 | 13.5 | 5.7 |
| —OH/Co | 0.0 | 4.0 | 7.9 | 0.0 | 1.9 | 3.4 | 5.3 | 0.0 | 2.0 | 4.2 | 3.1 |
| Temp °C. | 159 | 159 | 164 | 168 | 166 | 166 | 166 | 170 | 171 | 170 | 170 |
| % Yield KA | 58.9 | 47.7 | 47.4 | 64.5 | 69.0 | 56.3 | 54.2 | 67.1 | 64.5 | 53.5 | 54.4 |
| % Yield CHHP | 20.7 | 33.3 | 33.0 | 10.1 | 14.2 | 22.9 | 21.8 | 10.5 | 16.3 | 23.6 | 22.4 |
| CHHP/(CHHP + K + A) (by wt.) | 0.27 | 0.42 | 0.43 | 0.15 | 0.19 | 0.30 | 0.35 | 0.15 | 0.23 | 0.33 | 0.30 |
| % Conversion | 3.3 | 3.4 | 3.5 | 3.3 | 3.4 | 3.1 | 2.8 | 3.4 | 3.5 | 3.5 | 3.3 |

TABLE 2

| | F | 7 | 8 | G | 9 |
|---|---|---|---|---|---|
| Catalyst Conc. ppm Co | 0.50 | 0.50 | 0.50 | 0.50 | 0.50 |
| —OH/Co | 0.0 | 4.0 | 6.9 | 0.0 | 4.0 |
| % Yield KA | 43.0 | 37.2 | 33.4 | 55.7 | 43.9 |
| % Yield CHHP | 46.5 | 53.6 | 59.4 | 31.3 | 49.0 |
| CHHP/(CHHP + K + A) (by wt.) | 0.55 | 0.63 | 0.67 | 0.40 | 0.69 |
| % Conversion | 3.0 | 3.0 | 3.0 | 3.0 | 3.0 |

In the above tables, ppm are based on parts of product fluid exiting the reactor. Percent yields are expressed by mol % of component in the effluent versus mol % of cyclohexane consumed. Percent conversion is determined by cyclohexane consumed divided by cyclohexane exiting the oxidizer times 100.

Enhanced CHHP production is evidenced by increases in the weight ratio of CHHP to the sum of CHHP plus K and A, CHHP/(CHHP+K+A), as measured after the product fluid exits from the oxidizer. The weight of CHHP can be determined by iodometric titration, and the weight of K and A by gas chromatograph. As is apparent from the Tables, the presence of the phosphate ester in an amount that provides acid equivalents at the stoichiometric level of 2/1 —OH/Co or less provides little enhanced CHHP production over that obtainable in the absence of the phosphate ester, under a given set of process conditions such as catalyst concentration and temperature. When the oxidation is carried out according to the teachings of this invention using a —OH/Co ratio of at least 3/1, the CHHP/(CHHP+K+A) is significantly enhanced.

The product fluids with enhanced CHHP as obtained from the reactor in Examples 1–9 can subsequently be treated in a separate step to convert the CHHP to K and A.

To convert the CHHP to K and A, any one of a number of known processes may be used. Perhaps the best known is the catalytic thermal decomposition using a bed of solid catalyst as taught in the aforementioned U.S. Pat. No. 2,851,496 or as taught in U.S. Pat. No. 3,923,895, Costantini, et al., which specifies the use of a cyclohexane-soluble chromium derivative as catalyst in conjunction with a monoester or diester of ortho-phosphoric acid, such as di(2-ethylhexyl)ortho-phosphate.

The presence of the phosphate ester in the CHHP decomposition step is said to prevent buildup of deposits on the walls of the dehydroperoxidation reactor.

Other decomposition methods may also be employed such as caustic decomposition as taught in U.S. Pat. No. 4,238,415 of Bryan which specifies the use of a metal salt, normally of a transition metal, in the presence of an aqueous solution of an alkali metal hydroxide.

Other methods for converting the CHHP to K and A include hydrogenation using a noble metal catalyst such as palladium as taught in U.S. Pat. No. 3,927,103 of van de Moesdijk et al.

What is claimed is:

1. Process for the oxidation of cyclohexane to a product fluid consisting essentially of unreacted cyclohexane, cyclohexanone, cyclohexanol and cyclohexyl hydroperoxide, wherein a fluid containing cyclohexane and a cyclohexane-soluble catalyst selected from the group consisting of cobalt naphthenate, cobalt octoate, cobalt laurate, cobalt palmitate, cobalt stearate, cobalt linoleate, cobalt acetylacetonate and mixtures thereof in the amount of 0.1 to 5 parts cobalt per million parts of product fluid is oxidized by means of a gas containing molecular oxygen at a temperature in the range of 130°–180° C. in the presence of an ester of phosphoric acid having the formula

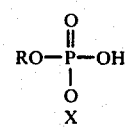

wherein R is selected from the group consisting of $C_4$–$C_{12}$ alkyl radicals and $C_5$–$C_8$ cycloalkyl radicals and X is H or R, said ester being present in an amount providing between about 3 to about 8 acid equivalents per atom of cobalt.

2. The process of claim 1 wherein the ester is present in an amount providing between 3 to 5 acid equivalents per atom of cobalt.

3. The process of claim 2 wherein the ester of phosphoric acid is di(2-ethylhexyl)phosphoric acid.

* * * * *